(12) United States Patent
Lendlein et al.

(10) Patent No.: US 8,834,522 B2
(45) Date of Patent: Sep. 16, 2014

(54) BIODEGRADABLE SHAPE MEMORY POLYMERIC SUTURES

(75) Inventors: Andreas Lendlein, Berlin (DE); Robert S Langer, Cambridge, MA (US)

(73) Assignee: Helmholtz-Zentrum Geestahacht Zentrum fur Material und Kustenforschung, Geesthacht (DE)

( * ) Notice: Subject to any disclaimer, the term of this patent is extended or adjusted under 35 U.S.C. 154(b) by 46 days.

(21) Appl. No.: 13/596,371

(22) Filed: Aug. 28, 2012

(65) Prior Publication Data

US 2012/0323274 A1     Dec. 20, 2012

Related U.S. Application Data

(62) Division of application No. 10/419,323, filed on Apr. 18, 2003, now Pat. No. 8,303,625.

(60) Provisional application No. 60/373,689, filed on Apr. 18, 2002.

(51) Int. Cl.
| | |
|---|---|
| *A61B 17/04* | (2006.01) |
| *A61L 29/14* | (2006.01) |
| *A61L 27/50* | (2006.01) |
| *A61L 31/14* | (2006.01) |
| *A61L 27/16* | (2006.01) |
| *A61L 17/10* | (2006.01) |
| *A61L 27/58* | (2006.01) |
| *A61L 17/14* | (2006.01) |
| *A61B 17/00* | (2006.01) |
| *A61B 17/06* | (2006.01) |

(52) U.S. Cl.
CPC . *A61B 17/06166* (2013.01); *A61B 2017/00867* (2013.01); *A61L 2400/16* (2013.01); *A61B 2017/0619* (2013.01); *A61L 29/14* (2013.01); *A61L 27/50* (2013.01); *A61L 31/148* (2013.01); *A61L 31/14* (2013.01); *A61L 29/148* (2013.01); *A61L 27/16* (2013.01); *A61L 17/10* (2013.01); *A61L 27/58* (2013.01); *A61B 2017/00004* (2013.01); *A61L 17/145* (2013.01)
USPC ............. 606/228; 606/230; 528/80; 528/272

(58) Field of Classification Search
USPC ......... 606/139, 144–148, 151–156, 222–232; 528/76, 80, 272
See application file for complete search history.

(56) References Cited

U.S. PATENT DOCUMENTS

| | | | |
|---|---|---|---|
| 3,867,190 A | | 2/1975 | Schmitt et al. |
| 5,234,006 A | * | 8/1993 | Eaton et al. .................. 128/898 |

(Continued)

OTHER PUBLICATIONS

A. Lendlein et al: "Hydroxy-telechelic copolyesters with well defined sequence structure through ring-opening polymerization", Macromol. Chem. Phys., vol. 201, Jul. 1, 2000.

(Continued)

*Primary Examiner* — Kathleen Holwerda
(74) *Attorney, Agent, or Firm* — VLP Law Group LLP; Kent H. Cheng

(57) ABSTRACT

Described herein are a group of degradable, thermoplastic polymers, which are able to change their shape after an increase temperature. Their shape memory capability enables bulky implants to be placed in the body through small incisions or to perform complex mechanical deformations automatically. The shape memory polymers are preferably biocompatible and can be biodegradable or non-degradable polymers. Preferably, the biodegradable polymer has a linear degradation rate. In a specifically preferred embodiment, the suture is formed of biodegradable polymer capable of forming a self-tightening knot. In a most preferred embodiment, the suture is used to close a wound or body scission.

12 Claims, 8 Drawing Sheets

(56) References Cited

U.S. PATENT DOCUMENTS

| | | | |
|---|---|---|---|
| 5,454,834 A * | 10/1995 | Boebel et al. | 606/228 |
| 5,618,313 A | 4/1997 | Roby et al. | |
| 5,626,611 A | 5/1997 | Liu et al. | |
| 5,651,377 A * | 7/1997 | O'Donnell, Jr. | 128/898 |
| 6,160,084 A * | 12/2000 | Langer et al. | 528/272 |
| 6,183,499 B1 | 2/2001 | Fischer et al. | |
| 6,262,127 B1 | 7/2001 | Acemoglu et al. | |
| 6,281,262 B1 | 8/2001 | Shikinami | |
| 6,388,043 B1 | 5/2002 | Langer et al. | |
| 6,881,766 B2 * | 4/2005 | Hain | 523/105 |

OTHER PUBLICATIONS

Bezwada R S et al: "Monocryl (R) suture, a new ultra-pliable absorbable monofilament suture", Biomaterials, Elsevier Science Publishers BV., vol. 16, Oct. 1, 1995.

* cited by examiner

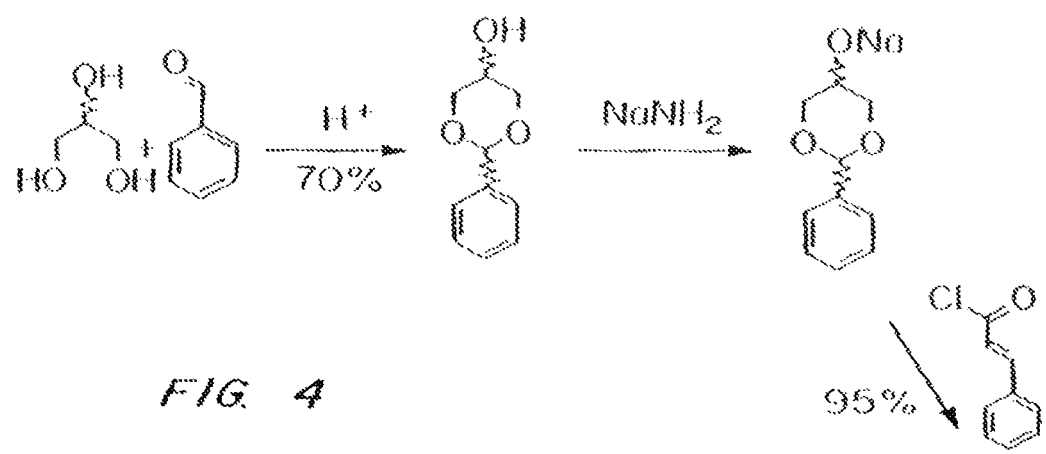
FIG. 4
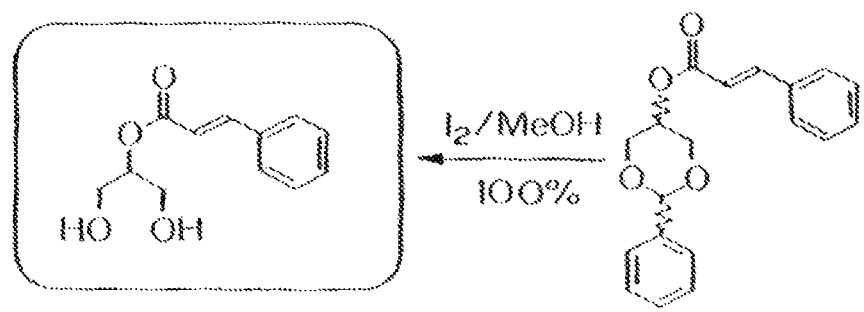

BIODEGRADABLE SHAPE MEMORY POLYMERIC SUTURES

CROSS REFERENCE TO RELATED APPLICATIONS

This application is a divisional of U.S. application Ser. No. 10/419,323, filed Apr. 18,2003, which claims the benefit of priority to U.S. Provisional application Ser. No. 60/373,689, filed Apr. 18, 2002, the contents of all of which are incorporated herein by reference.

FIELD OF THE INVENTION

This application is generally in the area of biodegradable shape memory polymeric devices, and more particularly to biodegradable shape memory polymeric sutures.

BACKGROUND OF THE INVENTION

Shape memory is the ability of a material to remember its original shape, either after mechanical deformation (FIG. 1), which is a one-way effect, or by cooling and heating (FIG. 2), which is a two-way effect. This phenomenon is based on a structural phase transformation.

The first materials known to have these properties were shape memory metal alloys (SMAs), including TiNi (Nitinol), CuZnAl, and FeNiAl alloys. The structure phase transformation of these materials is known as a martensitic transformation. These materials have been proposed for various uses, including vascular stents, medical guidewires, sutures, orthodontic wires, vibration dampers, pipe couplings, electrical connectors, thermostats, actuators, eyeglass frames, and brassiere underwires. For example, U.S. Pat. Nos. 5,002, 563, 5,766,218, and 5,281,236 describe various articles formed of shape memory alloys in various medical applications. Nonetheless, these materials have not yet been widely used, in past because they are relatively expensive.

Shape memory polymers (SMPs) are being developed to replace or augment the use of SMAs, in part because the polymers are light, high in shape recovery ability, easy to manipulate, and economical as compared with SMAs. In the literature, SMPs are generally characterized as phase segregated linear block copolymers having a hard segment and a soft segment. The hard segment is typically crystalline, with a defined melting point, and the soft segment is typically amorphous, with a defined glass transition temperature. In some embodiments, however, the hand segment is amorphous and has a glass transition temperature rather than a melting point. In other embodiments, the soft segment is crystalline and has a melting point rather than a glass transition temperature. The melting point or glass transition temperature of the soft segment is substantially less than the melting point or glass transition temperature of the hard segment.

When the SMP is heated above the melting point or glass transition temperature of the hard segment, the material can be shaped. This (original) shape can be memorized by cooling the SMP below the melting point or glass transition temperature of the hard segment. When the shaped SMP is cooled below the melting point or glass transition temperature of the soft segment while the shape is deformed, a new (temporary) shape is fixed. The original shape is recovered by heating the material above the melting point or glass transition temperature of the soft segment but below the melting point or glass transition temperature of the hard segment. In another method for setting a temporary shape, the material is deformed at a temperature lower than the melting point or glass transition temperature of the soft segment, resulting in stress and strain being absorbed by the soft segment. When the material is heated above the melting point or glass transition temperature of the soft segment, but below the melting point (or glass transition temperature) of the hard segment, the stresses and strains are relieved and the material returns to its original shape. The recovery of the original shape, which is induced by an increase in temperature, is called the thermal shape memory effect. Properties that describe the shape memory capabilities of a material are the shape recovery of the original shape and the shape fixity of the temporary shape.

Several physical properties of SMPs other than the ability to memorize shape are significantly altered in response to external changes in temperature and stress, particularly at the melting point or glass transition temperature of the soft segment. These properties include the elastic modulus, hardness, flexibility, vapor permeability, damping, index of refraction, and dielectric constant. The elastic modulus (the ratio of the stress in a body to the corresponding strain) of an SMP can change by a factor of up to 200 when heated above the melting point or glass transition temperature of the soft segment. Also, the hardness of the material changes dramatically when the soft segment is at or above its melting point or glass transition temperature. When the material is heated to a temperature above the melting point or glass transitions temperature of the soft segment, the damping ability can be up to five times higher than a conventional rubber product. The material can readily recover to its original molded shape following numerous thermal cycles, and can be heated above the melting point of the hard segment and reshaped and cooled to fix a new original shape.

Conventional shape memory polymers generally are segmented polyurethanes and have hard segments that include aromatic moieties. U.S. Pat. No. 5,145,935 to Hayashi, for example, discloses a shape memory polyurethane elastomer molded article formed from a polyurethane elastomer polymerized from a difunctional diiiosicyanate, a difunctional polyol, and a difunctional chain extender.

Examples of polymers used to prepare hard and soft segments of known SMPs include various polyethers, polyacrylates, polyamides, polysiloxanes, potyurethanes, polyether amides, polyurethane/ureas, polyether esters, and urethane/ butadiene copolymers. See, for example, U.S. Pat. No. 5,506, 300 to Ward et al.; U.S. Pat. No. 5,145,935 to Hayashi; U.S. Pat. No. 5,665,822 to Bitler et al.; and Gorden, "Applications of Shape Memory Polyurethanes," *Proceedings of the First International Conference on Shape Memory and Superelastic Technologies, SMST International Committee*, pp. 115-19 (1994).

Current approaches for implanting medical devices, many of which are polymeric in nature, often require complex surgery followed by device implantation. With the advent of minimally invasive surgery (J. G. Hunter, Ed., *Minimally invasive surgery* (McGraw Mill, N.Y., 1993)), it is possible to place small systems down laprascopes. However, there remains a challenge for one to implant a bulky device and/or knot a suture in a confined space. Moreover, Established synthetic, degradable suture materials are mainly aliphatic polyhydroxy acids showing bulk degradation. This degradation process can be split into several stages (A, Lendlein, *Chem. in unserer Zeit* 33, 279 (1999)), the first three of which are swelling, loss in molecular weight, and loss in sample mass.

U.S. Pat. No. 6,281,262 B1 to Shikinami and EP 1000958 by Takiron Co., Ltd. describe DL-lactide based polyester as shape-memory biodegradable and absorbable materials. The polyester can be made into various articles that, upon heating, can recover their respective original shapes. However, the degradation of L-lactide based polyesters shows a non-linear mass loss leading to a sudden release of potentially acidic degradation products from the bulk material, that may cause a strong inflammatory response (K. Fu, D. W. Pack, A. M. Klibanov, R. S. Langer, *Pharm Res* 17:1, 100 (2000)). High crystallinity of oligomer particles slows down degradation at the end of the process and leads to the formation of fibrous capsules in vivo (K. A. Hooper, N. D. Macon, J. Kobe, *J. Biomed. Mat. Res.* 32,443 (1998)).

A challenge in endoscopic surgery is the tying of a knot with instruments and sutures currently available to close an incision or open lumen. It is especially difficult to manipulate the suture in a way that the wound lips are pressed together under the right stress. When the knot is fixed with a force that is too strong, necrosis of the surrounding tissue may occur (J. Hoer, U. Klinge, A. Schachtrupp, Ch. Töns, V. Schumpelick, *Langenb. Arch. Surg* 386 218 (2001)). If the force is too weak, the formation of scar tissue which has poorer mechanical properties is observed, and may lead to the formation of hernias (N. C. F. Hodgson, R. A. Malthaner, T. Østbye, *Ann. Surg.* 231, 436 (2000)).

It therefore an object of the present invention to provide a biodegradable shape memory polymeric device that can be formed in a compressed temporary shape and then on demand be expanded to its permanent shape to fit as required.

It is another object of the present invention to provide a biodegradable implant that has a linear mass degradation rate in vivo. It is a further object of the present invention to provide a biodegradable shape memory polymeric suture that can be formed in a compressed temporary shape and then on demand be expanded to its permanent shape to fit as required.

It is still a further object of the present invention to provide a biodegradable shape memory polymeric suture that can be knotted in a confined space.

SUMMARY OF INVENTION

Described herein are a group of shape memory polymers which are capable of changing their shape after an increase in temperature. Their shape memory capability enables bulky implants to be placed in the body through small incisions or to perform complex mechanical deformations automatically. The shape memory polymers are preferably biocompatible and can be biodegradable or non-degradable polymers. Preferably, the biodegradable polymer has a linear degradation rate.

In one embodiment the compositions include at least one hard segment and at least one soft segment. The $T_{trans}$ of the hard segment is preferably between −40° C. and 270° C., between −40° C. and 200° C., between 30° C. and 150° C., or between 30° C. and 100° C. The soft segment has a $T_{trans}$ at least 10° C. lower than that of the hard segment(s), preferably in a range between −40° C. and 270° C. between −40° C. and 250° C., or between 0° C. and 200° C. At least one of the hard or soft segments can contain a crosslinkable group, and the segments can be linked by formation of an interpenetrating network or a semi-interpenetrating network, or by physical interactions of the segments. Objects can be formed into a given shape at a temperature above the $T_{trans}$ of the hard segment, and cooled to a temperature below the $T_{trans}$ of the soft segment. If the object is subsequently formed into a second shape, the object can return to its original shape by heating the object above the $T_{trans}$ of the soft segment and below the $T_{trans}$ of the hard segment.

Articles for various applications can be formed of the shape memory polymer. In a preferred embodiment, the implant is a suture. The suture is capable of forming self-tightening knot. In a specifically preferred embodiment, the degradable shape memory polymeric suture can be knotted in a confined space. In a most preferred embodiment, the suture is used to close a wound or body scission. The suture can be Therapeutic, prophylactic, and diagnostic agents can be incorporated within the disclosed shape memory polymer compositions to form articles such as suture for medical applications.

DESCRIPTION OF THE DRAWINGS

FIG. 4 is a diagram of a reaction sequence for the synthesis of a preferred photocrosslinker.

DETAILED DESCRIPTION OF THE INVENTION

Figure 1:
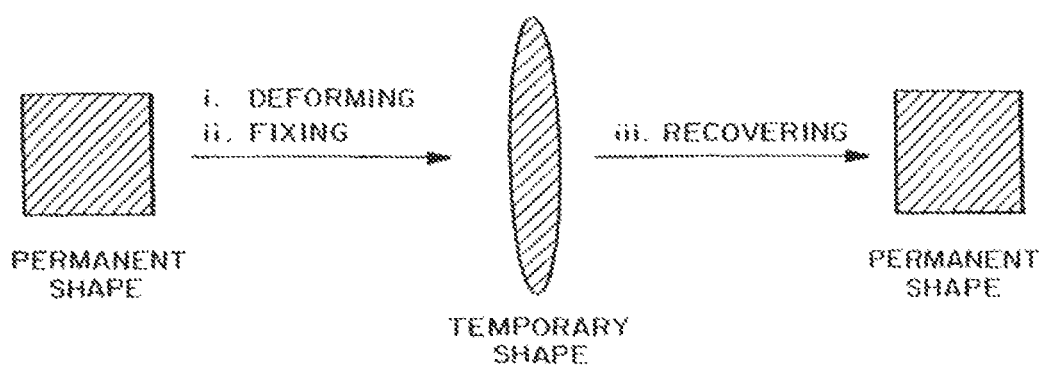
FIG. 1 is an illustration of the one-way shape memory effect.
Figure 2:
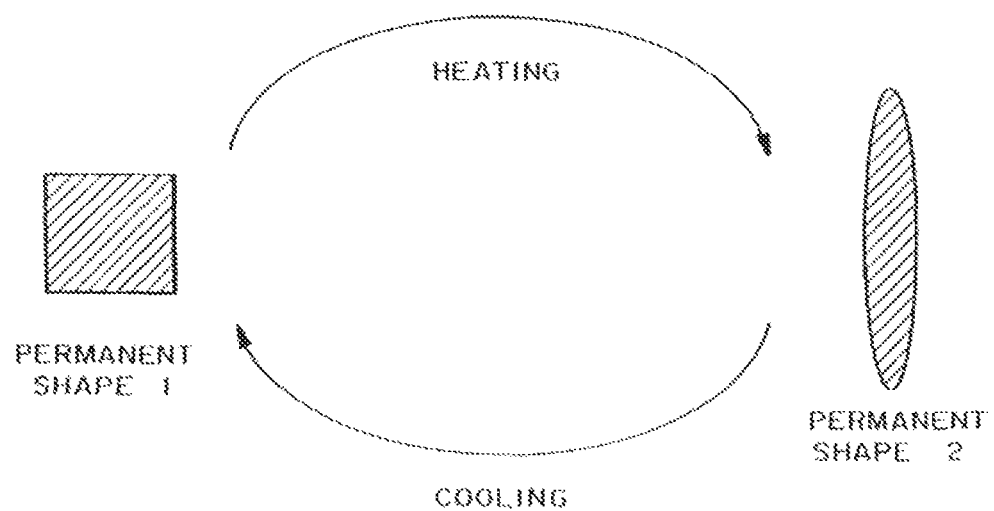
FIG. 2 is an illustration of the two-way (thermal) shape memory effect.

Shape memory polymer compositions, articles of manufacture thereof including sutures, and methods of preparation and use thereof are described. The shape memory polymer composition can be biodegradable or non-degradable.

Definitions

As used herein, the term "biodegradable" refers to materials that are bioresorbable and/or degrade and/or break down by mechanical degradation upon interaction with a physiological environment into components that are metabolizable or excretable, over a period of time from minutes to three years, preferably less than one year, while maintaining the requisite structural integrity. As used herein in reference to polymers, the term "degrade" refer to cleavage of the polymer chain, such that the molecular weight stays approximately constant at the oligomer level and particles of polymer remain following degradation. The term "completely degrade" refers to cleavage of the polymer at the molecular level such that there is essentially complete mass loss. The term "degrade" as used herein includes "completely degrade" unless otherwise indicated. The term "linear degradation behavior" as used herein refers to a linear mass loss of the sample during degradation resulting in a continuous release of degradation products.

A polymer is a shape memory polymer if the original shape of the polymer is recovered by heating it above a shape recovering temperature (defined as the $T_{trans}$ of a soft segment) even if the original molded shape of the polymer is destroyed mechanically at a lower temperature than the shape recovering temperature, or if the memorized shape is recoverable by application of another stimulus.

As used herein, the term "segment" refers to a block or sequence of polymer forming part of the shape memory polymer.

As used herein, the terms hard segment and soft segment are relative terms, relating to the $T_{trans}$ of the segments. The hard segment(s) has a higher $T_{trans}$ than the soft segment(s). The shape memory polymers can include at least one hard segment and at least one soft segment, or can include at least one kind of soft segment wherein at least one kind of the soft segments are crosslinked, without the presence of a hard segment.

The hard segments can be linear oligomers or polymers, and can be cyclic compounds, such as crown ethers, cyclic di-, tri-, or oligopetides, and cyclic oligo(ester amides).

The physical interaction between hard segments can be based on charge transfer complexes, hydrogen bonds, or other interactions, since some segments have melting temperatures that are higher than the degradation temperature. In these cases, there is no melting or glass transition temperature for the segment. A non-thermal mechanism, such as a solvent, is required to change the segment bonding.

The ratio by weight of the hard segment:soft segments is between about 5:95 and 95:5, preferably between 20:80 and 80:20.

Shape Memory Polymeric Compositions

Thermoplastic shape memory materials are shaped/molded to a desired shape above the $T_{trans}$ of the hard segment(s) and cooled down to a temperature below the shape recovering temperature, where the polymer may undergo mechanical deformation and strains are generated in the polymer. The original shape of the deformed polymers is recovered by heating the polymers to a temperature higher than their shape recovering temperature. Above this temperature, the strains in the polymer are relieved, allowing the polymer to return to its original shape. In contrast, thermoset shape memory materials are shaped/molded to a desired shape before the macromonomers used to form the thermoset polymers are polymerized. After the shape has been fixed, the macromonomers are polymerized.

The polymer compositions are preferably compressible by at least one percent or expandable by at least five one of the original thickness at a temperature below the shape recovering temperature, with the deformation being fixed by application of a stimulus such as heat, light, ultrasound, magnetic fields or electric fields. In some embodiments, the materials show a ratio of recovery of 98%.

When significant stress is applied, resulting in an enforced mechanical deformation at a temperature lower than the shape recovering temperature, strains are retained in the soft segments or amorphous regions, and bulky shape change is kept even after the partial liberation of strain by the elasticity of the polymer. If the configuration of the molecular chains is disturbed by influencing the regulated arrangement of molecular chains at a temperature lower than the glass transition temperature, rearrangement of the molecular chains is assumed to occur through the increase of the volume size and the decrease of the free volume content. The original shape is recovered by the contraction of the hard segment aggregates by the elevation of the temperature according to rigid control of chain conformations and the shape of the polymer is restored to the memorized shape.

In addition to changes in state from a solid to liquid state (melting point or glass transition temperature), hard or soft segments can undergo ionic interactions involving polyelectrolyte segments or supramolecular effects based on highly organized hydrogen bonds. The SM polymer can also undergo solid state to solid state transitions (e.g. change in morphology). Solid state to solid state transitions are well known to those of skill in the art, e.g. in poly(styrene-block-butadiene).

Various changes can take place to the structure of an object formed using the shape memory polymers. If the objects are three dimensional objects, the changes in shape can be two dimensional. If the objects are essentially two dimensional objects, such as fibers, then the changes in shape can be one dimensional, such as along the length. The thermal and electrical conductivity of the materials can also change in response to changes in temperature.

The moisture permeability of the compositions can be varied, especially when the polymer is formed into a thin film (i.e., less than about 10 μm). Some polymer compositions, in their original shape, have a sufficient permeability such that molecules of water vapor can be transmitted through the polymer film, while water molecules are not large enough to penetrate the polymer film. The resulting materials have low moisture permeability at temperatures below room temperature and high moisture permeability at temperatures above room temperature.

Stimuli other than temperature can be used to induce shape changes. As described with reference to certain embodiments below, the shape changes can be elicited by exposure to light activation or an agent such as an ion which alters the interpolymer bonds.

I. Polymer Segments

The segments preferably are oligomers. As used herein, the term "oligomer" refers to a linear chain molecule having a molecular weight up to 15,000 Dalton.

The polymers are selected based on the desired glass transition temperature(s) (if at least one segment is amorphous) or the melting point(s) (if at least one segment is crystalline), which in turn is based on the desired applications, taking into consideration the environment of use. Preferably, the number average molecular weight of the polymer block is greater than 400, and is preferably in the range of between 500 and 15,000.

The transition temperature at which the polymer abruptly becomes soft and deforms can be controlled by changing the monomer composition and the kind of monomer, which enables one to adjust the shape memory effect at a desired temperature.

The thermal properties of the polymers can be detected, for example, by dynamic mechanical thermoanalysis or differential scanning calorimetry (DSC) studies. In addition the melting point can be determined using a standard melting point apparatus.

1. Thermoset or thermoplastic polymers.

The polymers can be thermoset or thermoplastic polymers, although thermoplastic polymers may be preferred due to their ease of molding.

Preferably, the degree of crystallinity of the polymer or polymeric block(s) is between 3 and 80%, more preferably between 3 and 60%. When the degree of crystallinity is greater than 80% while all soft segments are amorphous, the resulting polymer composition has poor shape memory characteristics.

The tensile modules of the polymers below the $T_{trans}$ is typically between 50 MPs and 2 GPa (gigapascals), whereas the tensile modulus of the polymers above the $T_{trans}$ is typically between 1 and 500 MPa. Preferably, the ratio of elastic modulus above and below the $T_{trans}$ is 20 or more. The higher the ratio, the better the shape memory of the resulting polymer composition.

The polymer segments can be natural or synthetic, although synthetic polymers are preferred. The polymer segments can be biodegradable or non-biodegradable, although the resulting SMP composition is biodegradable biocompatible polymers are particularly preferred for medical applications. In general, these materials degrade by hydrolysis, by exposure to water or enzymes under physiological conditions, by surface erosion, bulk erosion, or a combination thereof. Non-biodegradable polymers used for medical applications preferably do not include aromatic groups, other than those present in naturally occurring amino acids.

Representative natural polymer segments or polymers include proteins such as zein, modified zein, casein, gelatin, gluten, serum albumin, and collagen, and polysaccharides such as alginate, celluloses, dextrans, pullulate, and polyhyaluronic acid, as well as chitin, poly(3-hydroxyalkanoate)s, especially poly(β-hydroxybutyrate), poly(3-hydroxyoctanoate) and poly(3-hydroxyfatty acids).

Representative natural biodegradable polymer segments or polymers include polysaccharides such as alginate, dextran, cellulose, collagen, and chemical derivatives thereof (substitutions, additions of chemical groups, for example, alkyl, alkylene, hydroxylations, oxidations, and other modifications routinely made by those skilled in the art), and proteins such as albumin, zein and copolymers and blends thereof, alone or in combination with synthetic polymers.

Representative synthetic polymer blocks include polyphosphazenes, poly(vinyl alcohols), polyamides, polyester amides, poly(amino acid)s, synthetic poly(amino acids), polyanhydrides, polycarbonates, polyacrylates, polyalkylenes, polyacrylamides, polyalkylene glycols, polyalkylene oxides, polyalkylene terephthalates, polyortho esters, polyvinyl ethers, polyvinyl esters, polyvinyl halides, polyvinylpyrrolidone, polyesters, polylactides, polyglycolides, polysiloxanes, polyurethanes and copolymers thereof.

Examples of suitable polyacrylates include poly/(methyl methacrylate), poly(ethyl methacrylate), poly(butyl methacrylate), poly(isobutyl methacrylate), poly(hexyl methacrylate), poly(isodecyl methacrylate), poly(lauryl methacrylate), poly(phenyl methacrylate), poly(methyl acrylate), poly(isopropyl acrylate), poly(isobutyl acrylate) and poly(octadecyl acrylate).

Synthetically modified natural polymers include cellulose derivatives such as alkyl celluloses, hydroxyalkyl celluloses, cellulose ethers, cellulose esters, nitrocelluloses, and chitosan. Examples of suitable cellulose derivatives include methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxymethyl cellulose, cellulose triacetate and cellulose sulfate sodium salt. These are collectively referred to herein as "celluloses".

Representative synthetic degradable polymer segments or polymers include polyhydroxy acids, such as polylactides, polyglycolides and copolymers thereof; poly(ethylene terephthalate); poly(hydroxybutyric acid); poly(hydroxyvaleric acid); poly[lactide-co-(ε-caprolactone)]; poly[glycolide-co-(ε-caprolactone)]; polycarbonates, poly(pseudo amino acids); poly(amino acids); poly(hydroxyalkanoate)s; polyanhydrides; polyortho esters; and blends and copolymers thereof.

Examples of non-biodegradable polymer segments or polymers include ethylene vinyl acetate, poly(meth)acrylic acid, polyamides, polyethylene, polypropylene, polystyrene, polyvinyl chloride, polyvinylphenol, and copolymers and mixtures thereof.

Rapidly bioerodible polymers such as poly(lactide-co-glycolide)s, polyanhydrides, and polyorthoesters, which have carboxylic groups exposed on the external surface as the smooth surface of the polymer erodes, also can be used. In addition, polymers containing labile bonds, such as polyanhydrides and polyesters, are well known for their hydrolytic reactivity. Their hydrolytic degradation rates can generally be altered by simple changes in the polymer backbone and their sequence structure.

Various polymers, such as polyacetylene and polypyrrole, are conducting polymers. These materials are particularly preferred for uses in which electrical conductance is important. Examples of these uses include tissue engineering and any biomedical application where cell growth is to he stimulated. These materials may find particular utility in the field of computer science, as they are able to absorb heat without increasing in temperature better than SMAs. Conducting shape memory polymers are useful in the field of tissue engineering to stimulate the growth of tissue, for example, nerve tissue.

II. Assembly of Polymer Segments

The shape memory polymer include one or more hard segments and one or more soft segments, wherein at least one of the hard or soft segments is biodegradable or at least one of the hard or soft segments is linked to another hard or soft segment via a biodegradable linkage. Representative biodegradable linkages include ester-, amide-, anhydride-, carbonate-, or orthoester linkages. One exemplary biodegradable linkage is 2,2(4),4-trimethylhexanediisocyanate.

1. Polymer Structures

The shape memory effect is based on the polymer morphology. With respect to thermoplastic elastomers, the original shape of an object is fixed by physical crosslinks caused by the hard segment. With respect to thermoset polymers, the soft segments are covalently crosslinked instead of having hard segments. The original shape is set by the crosslinking process.

In contrast to prior art segmented polyurethane SMPs, the segments of the compositions described herein need not be linear. The segments can be partially grafted or attached in dendremeric side groups.

A. Thermoplastic and Thermoelastic Polymers

Figure 3:
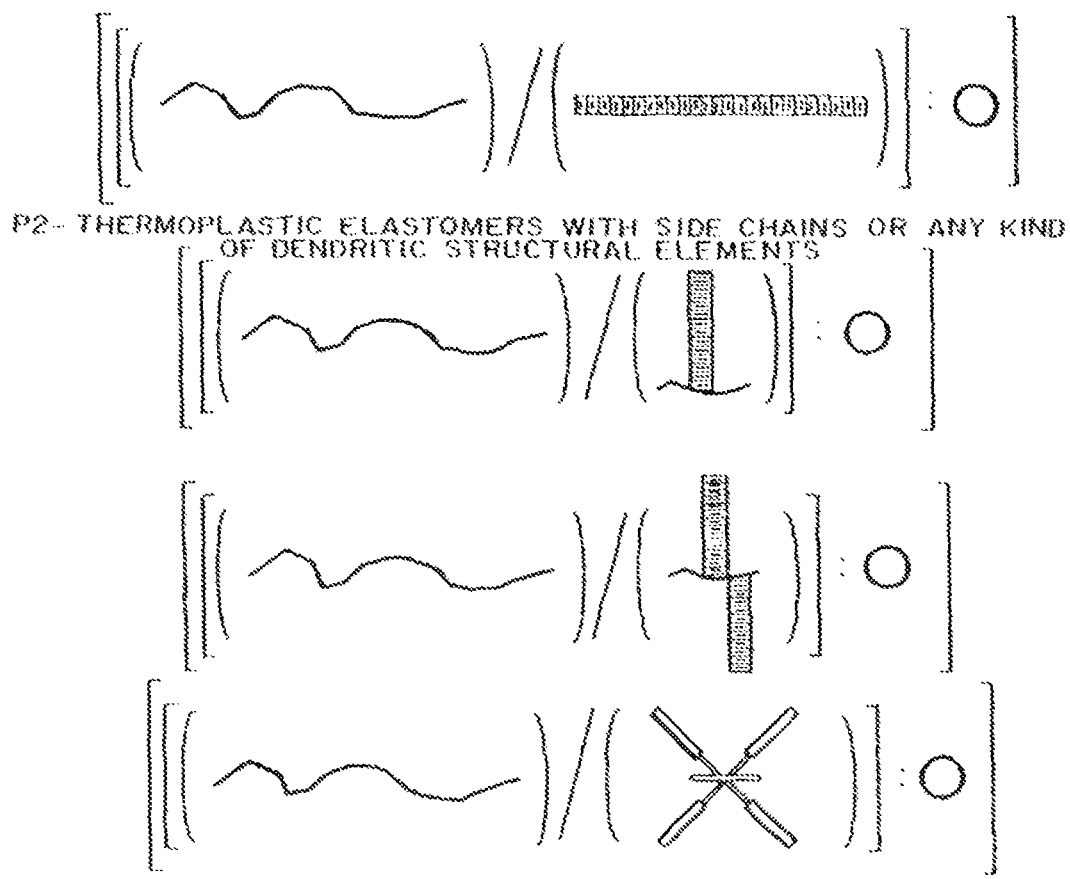
FIG. 3 is an illustration of combinations of suitable classes of thermoplastic materials.

The polymers can be in the form of linear diblock-, triblock-, tetrablock-, or multiblock copolymers, branch or graft polymers, thermoplastic elastomers, which contain dendritic structures, and blends thereof. FIG. 3 illustrates some of the combinations of suitable classes of thermoplastic materials forming the hard and soil segments. The thermoplastic shape memory polymer composition also can be a blend of one or more homo- or co-polymer with one or more diblock-, triblock-, tetrablock-, or multiblock copolymers, branch or graft polymers. These types of polymers are well known to those of skill in the art.

As used herein, the term "degradable thermoset" refers to (i) thermosets SMPs containing only one soft segment, which contains cleavable bonds, and (ii) thermosets containing more than one soft segment, wherein at least one soft segment is degradable or wherein the different soft segments are connected by cleavable bonds. There are four different types of thermoset polymers that have shape memory capability. These include polymer networks, semi-interpenetrating networks, interpenetrating networks, and mixed-interpenetrating networks.

i. Polymer Networks

A polymer network is prepared by covalently crosslinking macromonomers, i.e., polymers which contain polymerizable end-groups such as carbon-carbon double bonds. The polymerization process can be induced by using light or heat sensitive initiators or by curing with ultraviolet light ("UV-light") without an initiator. Shape memory polymer networks are prepared by cross-linking one or more soft segments which correspond to one or more thermal transitions.

In an embodiment preferred for biomedical applications, the crosslinking is performed using a photocrosslinker and requires no chemical initiator. The photocrosslinker advantageously eliminates the need for initiator molecules, which may be toxic. FIG. 4 is a diagram of a reaction sequence for the synthesis of a preferred photocrosslinker, which produces an overall yield of about 65%.

ii. Interpenetrating Networks

Interpenetrating networks ("IPN") are defined as networks where two components are crosslinked, but net to each other. The original shape is determined by the network with the highest crosslink density and the highest mechanical strength. The material has at least two $T_{trans}$ corresponding to the different soft segments of both networks.

iii. Mixed Interpenetrating Network

A mixed IPN includes at least one physically crosslinked polymer network (a thermoplastic polymer) and at least one covalently crosslinked polymer network (a thermoset polymer) that cannot be separated by any physical methods. The original shape is set by the covalently crosslinked network. The temporary shapes correspond to the $T_{trans}$ of the soft segments and the $T_{trans}$ of the hard segment of the thermoplastic elastomer component.

A particularly preferred mixed interpenetrating network is prepared by polymerizing a reactive macromonomer in the presence of a thermoplastic polymer, for example, by the photopolymerization of carbon-carbon double bonds. In this embodiment, the ratio by weight of thermoset polymer to thermoplastic polymer is preferably between 5:95 and 95:5, more preferably, between 28:80 and 80:20.

iv. Semi-Interpenetrating Networks

Semi-Interpenetrating networks ("semi-IPN ") are defined as two independent components, where one component is a crosslinked polymer (a polymer network) and the other component is a non-cross linked polymer (a homopolymer or copolymer), wherein the components cannot be separated by physical methods. The semi-IPN has at least one thermal transition corresponding to the soft segment(s) and the homo- or co-polymer components. The crosslinked polymer preferably constitutes between about 10 and 90% by weight of the semi-interpenetrating network composition.

v. Polymer Blends

In a preferred embodiment, the shape memory polymer compositions described herein are formed of a biodegradable polymer blend. As used herein, a "biodegradable polymer blend" is a blend having at least one biodegradable polymer.

The shape memory polymers can exist as physical mixtures of thermoplastic polymers. In one embodiment, a shape memory polymer composition can be prepared by interacting or blending two thermoplastic polymers. The polymers can be semicrystalline homopolymers, semicrystalline copolymers, thermoplastic elastomers with linear chains, thermoplastic elastomers with side chains or any kind of dendritic structural elements, and branched copolymers, and these can be blended in any combination thereof.

For example, a multiblock copolymer with a hard segment with a relatively high $T_{trans}$ and a soft segment with a relatively low $T_{trans}$ can be mixed or blended with a second multiblock copolymer with a hard segment with a relatively low $T_{trans}$ and the same soft segment as that in the first multiblock copolymer. The soft segments in both multiblock copolymers are identical, so the polymers are miscible in each other when the soft segments are melted. There are three transition temperatures in the resulting blend—that of first hard segment, that of the second hard segment, and that of the soft segment. Accordingly, these materials are able to memorize two different shapes. The mechanical properties of these polymers can be adjusted by the changing the weight ratio of the two polymers.

Other kinds of blends of at least two multiblock copolymers, in which at least one of the segments is miscible with at least one of the segments of the other multiblock copolymers, can be prepared. If two different segments are miscible and build one domain together, then the thermal transition of this domain depends on the weight content of the two segments. The maximum number of memorized shapes results from the number of thermal transitions of the blend.

Shape memory blends may have better shape memory capabilities than the blend components alone. Shape memory blends are composed of at least one multiblock copolymer and at least one homo- or copolymer. In principle di-, tri, tetra-block copolymers can be used instead of a multiblock copolymer.

Shape memory blends are highly useful in it industrial applications, since a broad range of mechanical, thermal, and shape memory capabilities can be obtained from only two or three basic polymers by blending them in different weight ratios. A twin screw extruder is an example of standard process equipment mat could be used to mix the components and process the blend.

III. Methods of Making the SMPs

The polymers described above are either commercially available or can be synthesized using routine chemistry. Those of skill in the art can readily prepare the polymers using known chemistry. Example 1 below describes experimental procedures used to prepare the SMPs.

IV. Methods of Shaping the SMP Compositions

The compositions cars be formed into a first shape under appropriate conditions, for example, at a temperature above the $T_{trans}$ of the hard segments, and allowed to cool below the $T_{trans}$ of the soft segment(s). Standard techniques are extrusion and injection molding. Optionally, the object can be re-formed into a second shape. Upon application of heat or other appropriate set of conditions, the object returns to original shape.

Figure 5:
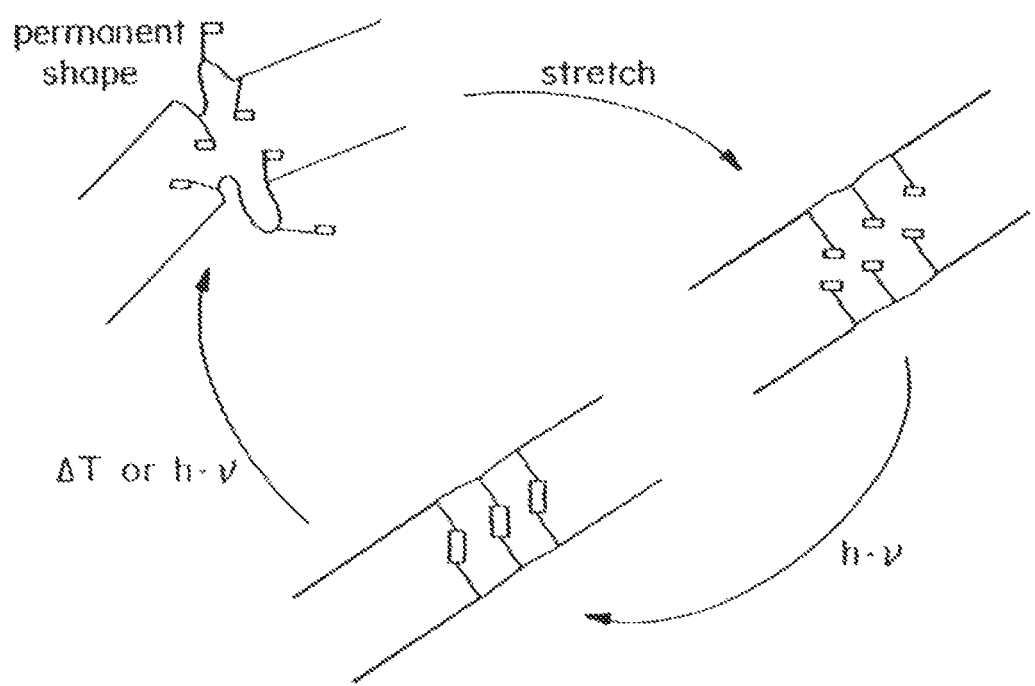
FIG. 5 is an illustration of a photoinduced shape memory effect.

Thermoset polymers can be prepared by extruding the pre-polymerized material (macromonomers), and fixing the original shape at a temperature above the $T_{trans}$ of the thermoset polymer, for example, by photocuring reactive groups on the monomer. The temporary shape is fixed by cooling the material below $T_{trans}$ after deforming the material. FIG. 5 illustrates a photoinduced shape memory effect.

The crosslinking also can be performed in a solution of the macromonomers. Use solvent is removed from the formed gel in a subsequent step.

Those compositions formed of thermoplastic polymers can be blown, extruded into sheets or shaped by injection molding, for example, to form fibers. The compositions can also be shaped by other methods known to those of skill in the art for shaping solid objects, for example, laser ablation, micromachining, use of a hot wire, and by CAD/CAM (computer aided design/computer aided manufacture) processes. These processes are preferred for shaping thermoset polymers.

The polymer compositions can be combined with fillers, reinforcement materials, radioimaging materials, excipients or other materials as needed for a particular implant application. Examples of fillers include calcium-sodium-metaphosphate which is described in U.S. Pat. No. 5,108,755, the disclosure of which is incorporated herein by reference. Those of skill in the art can readily determine a suitable amount of these materials to include in the compositions.

V. Therapeutic, Prophylactic, and Diagnostic Applications

Any of a variety of therapeutic, prophylactic and/or diagnostic agents can be incorporated within the polymer, compositions, which can locally or systemically deliver the incorporated agents following administration to a patient.

1. Therapeutic and Prophylactic Applications

Any of a variety of therapeutic agents can be incorporated within the compositions, for local or systemic delivery of the incorporated agents following administration to a patient. Examples include synthetic inorganic and organic compounds or molecules, proteins and peptides, polysaccharides and other sugars, lipids, and nucleic acid molecules having therapeutic, prophylactic or diagnostic activities. Nucleic acid molecules include genes, plasmid DNA, naked DNA, antisense molecules which bind to complementary DNA to inhibit transcription, ribozymes and ribozyme guide sequences. The agents to be incorporated can have a variety of biological activities, such as vasoactive agents, neuroactive agents, hormones, growth factors, cytokines, anaesthetics, steroids, anticoagulants, anti-inflammatories, immunomodulating agents, cytotoxic agents, prophylactic agents, antibiotics, antivirals, antisense, antigens, and antibodies. In some instances, the proteins may be antibodies or antigens which otherwise would have to he administered by injection to elicit an appropriate response. Proteins are defined as consisting of 100 amino acid residues or more; peptides are less than 100 amino acid residues. Unless otherwise stated, the term protein refers to both proteins and peptides. Polysaccharides, such as heparin, can also be administered. Compounds with a wide range of molecular weight, for example, between 10 and 500,000 grams per mole, can be encapsulated.

2. Diagnostic Applications

Any biocompatible or pharmacologically acceptable gas can be incorporated into particles formed of the polymer compositions or trapped in the pores of such particles using technology known to those skilled in the art. The term gas refers to any compound which is a gas or capable of forming a gas at the temperature at which imaging is being performed.

Other imaging agents which may be utilized include commercially available agents used in positron emission tomography (PET), computer assisted tomography (CAT), single photon emission computerized tomography, x-ray, fluoroscopy, and magnetic resonance imaging (MRI).

Examples of suitable materials for use as contrast agents in MRI include the gadolinium chelates currently available, such as diethylene triamine pentacetic acid (DTPA) and gadopentotate dimeglumine, as well as iron, magnesium, manganese, copper and chromium.

Examples of materials useful for CAT and x-rays include iodine based materials for intravenous administration, such as ionic monomers typified by diatrizoate and iothalamate, non-ionic monomers such as iopamidol, isohexol, and ioversol, non-ionic dimers, such as iotrol and iodixanol, and ionic dimers, for example, ioxagalte.

VII. Articles and Devices for Biomedical Applications

The SMP compositions can be used to prepare numerous articles of manufacture, for use in biomedical and other applications. For Example, the polymer compositions can be used to prepare articles of manufacture for use in biomedical applications. For example, sutures, orthodontic materials, bone screws, nails, plates, catheters, tubes, films, stents, orthopedic braces, splints, tape for preparing casts, and scaffolds for tissue engineering, contact lenses, drug delivery devices, implants, and thermal indicators, can be prepared.

The SMP compositions are preferably prepared from biocompatible polymers. The biocompatible polymer can be biodegradable or non-biodegradable. Preferably, the SMP compositions are formed of biodegradable polymers. Biodegradable polymers degrade at a controlled rate depending on the composition and crosslinking of the polymer. Degradable polymeric implants eliminate the need for implant retrieval and can be used simultaneously to deliver therapeutic agents.

The materials can be used in many applications requiring load-bearing capacities and controlled degradation. The polymer compositions can be formed into the shape of an implant which can be implanted within the body to serve a mechanical function. Examples of such implants include sutures, rods, pins, screws, plates and anatomical shapes.

A particularly preferred use of the compositions is to prepare sutures that have a rigid enough composition to provide for ease of insertion, but upon attaining body temperature, soften and form a second shape that is more comfortable for the patient while still allowing healing.

Sutures can be degradable (resorbable) or non-degradable. The sutures can be monofilament or multifilament. Braided multifilaments are characterized by a higher flexibility but have a higher roughness than monofilaments. To get smooth multifilaments often a coating is applied on the suture. Sutures can be made according to the methods available in the art. In addition, various methods for improving the properties of a suture are also well documented. For example, EP 0908 142 A2 by Ethicon Inc. describes a method for improving knot strength of a polymeric suture.

Exemplary resorbable sutures available in the market place are: Dexon II: homopolymer of glycolide, multifilament (Braun Surgical GmbH bzw. United States Surgical Corporation, North Haven, Conn.); Vicryl: copolymer of glycoside and lactide, multifilament (Ethicon, Inc., Sommerville, N.J.); Polysorb: copolymer of glycolide and lactide, multifilament (United States Surgical Corporation, North Haven, Conn.); PDS: homopolymer of p-dioxanone, monofilament (Ethicon, Inc., Sommerville, N.J.); Maxon: monofilament (United States Surgical Corporation, North Haven, Conn.); Biosyn: copolymer of p-dioxanone, trimethylencarbonate and glycoside, monofilament; (United States Surgical Corporation, North Haven, Conn.); Monocryl: block copolymer of glycoside and ε-caprolactone, monofilament (Ethicon, Inc., Sommerville, N.J.); and Bondek: homopolymer of diglycolide (Deknatel). These sutures can be readily prepared using the SMP materials described herein.

The sutures described herein have high flexibility, high tensile strength, suppleness, and controlled degradability. The use of a certain suture and the suture technique depend on the kind of tissue and the wound. The exact repositioning of the tissue interfaces is important to obtain the best wound healing. One of ordinary skill in the art would know which suture to use.

The self-tightening sutures can be made of SMP materials which are degradable or non-degradable. The SMP material can be thermoplastics or networks or blends. The suture can be monofilament or multifilament, non-coated or coated. The suture can be stretched and programmed uniform or non-uniform.

Sutures can have diameters of different range. In one embodiment, the sutures are mono-filament sutures preferably have a diameter about or less than 50 µm suitable for use in micro surgery.

In the multi-filaments, the single monofilaments can differ in the kind of filaments, degradation behaviour, mechanical properties, diameter, shape memory properties, programming, number of programmed shapes.

Figure 6A:
FIG. 6A shows the change of the texture of one filament in a shape memory multifilament suture.

In one embodiment, the filaments in the multifilament suture formed of shape memory compositions described herein can be all programmed substantially alike. "Programmed substantially alike" means that the filaments in a multifilament suture are programmed alike concerning the degree of stretching or the degree of three dimensional torsion or bending or a combination. In another embodiment, the filaments in the multifilament suture formed of shape memory compositions described herein can be programmed differently. "Programmed substantially differently" means that the filaments in a multifilament suture differ from each other concerning the degree of stretching or the degree of torsion or bending or a combination. This different programming of the filaments in a multifilament suture allows additional deformations responsive to different $T_{trans}$ in one filament or different filaments. Response to the change of temperature allows the change of the texture of the multifilament suture formed of differently programmed filaments (FIG. 6A).

The multifilament sutures can be made of a combination filaments formed of bio-degradable shape memory compositions and filaments formed of non-degradable shape memory compositions. For sutures used its fields of application that need non-degradable suture materials, e.g. sewing nerve fibers, minimal usage of degradable shape memory materials can be used to form the filaments of the sutures. Alternatively, the sutures can be formed of a predominant number of filaments formed of non-degradable shape memory compositions and a minimal number of filaments formed of biodegradable shape memory compositions. Variation of the ratio of the filaments of biodegradable shape memory material over filaments of non-degradable shape memory material allows the formation of sutures suitable for use in different applications. The ratio of the filaments of biodegradable shape memory material over filaments of non-degradable shape memory material can be in a range from, for example, about 0.5/99.5 to 99.5/0.5, 5/95 to 95/5, 10/90 to 90/10, 20/80 to 80/20, 30/70 to 70/30, 40/60 to 60/40 or 50/50.

Figure 6B:
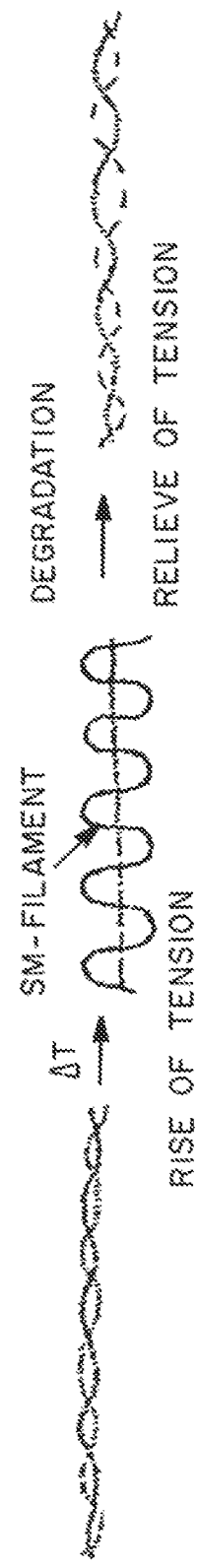
FIG. 6B shows the reversion of the shape memory effect of a suture by degradation of the shape memory filament.

Multifilament sutures formed of a combination of bio-degradable and non-degradable shape memory materials allow one to control the deformation of the sutures. If a deformation is caused by the degradable shape memory-filament, it can be reversed by degradation of the shape memory-filament (FIG. 6B).

The shame memory polymer composition described herein can be used as a coating on an already established suture material. The allows the addition of mechanical deformation (SM-effect) by the coating to the existing suture. Coating may be a covalent shape memory network or thermoplastic.

The shape memory sutures including monofilament and multifilament sutures described herein can be formed of or coated with shape memory polymers loaded with an agent such therapeutic, prophylactic and diagnostic agents described herein. In one example, the agent is a therapeutic agent such as disinfectant or antibiotic. Release of the agent in the sutures in vivo is accelerated at a temperature exceeding $T_{trans}$.

VII. Methods of Use

Certain articles of manufacture are designed to hold their intended shape unless acted upon in a manner inconsistent with their normal use. These articles of manufacture are to be used in their intended shape and repaired, for example, by application of heat, once they are damaged.

Other articles of manufacture are designed to be used such that the first shape is intended for an initial use, and a second shape is intended for a subsequent use. Examples of these include biomedical devices which can form a second shape upon reaching at body temperature, or upon application of an external stimulus which heats the device above body temperature.

Still other articles of manufacture are designed to be used such that their shape changes in reaction to, or adjustment to, changes in temperature, such as thermosensers in medical devices.

In one embodiment, the article is used as a suture for closing a body wound or body scission. The method of closing a wound or body scission generally includes the steps of (1) providing a suture formed of a shape memory polymer; (2) forming a loose knot of the suture; and (3) heating the suture to close the wound or body scission.

Figure 6C:
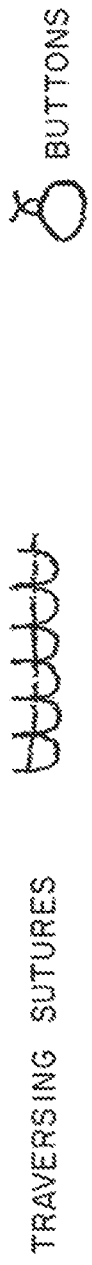
FIG. 6C illustrates a shape memory traversing suture and a shape memory button.

The sutures described herein are useful in many application. For example, the suture can be used in the form of contracting filament for wound closure. In the application, one can stitch loosely with the suture material and form a knot, and then warm up the stitch with an energy source such as IR-light. The suture then contracts, allowing the application of a defined tension to the wound edges. This allows the optimum healing of the wound. Control of the tension by for example chemical composition responsive to strength of the programmed elongation. Sutures in the contracting filament form are also useful in the non-minimally invasive area as traversing sutures and buttons (FIG. 6C).

The sutures of shape memory composition described herein can facilitate a predetermined three-dimensional movement in minimally invasive as well as in complex, conservatively executed surgery. The guidance of the suture in minimally invasive as well as in complex, conservatively executed surgery can be extremely extensive and difficult. The suture can be subject to three-dimensional deformation prior to use to guide the suture arise automatically in application by activating the SM-effect.

A minimally invasive surgery is a surgical technique to treat, cut, sew, etc, internal tissue or close deep wounds, wherein only small incisions on outer tissue are required. Small tubes (laprascopes) are put through the small incisions and the surgeon inserts his surgical instruments through the tubes. This technique requires special surgical instruments. This technique is used in cardiovascular, orthopedic, obstetric surgery etc. (see, tor example, J. G. Hunter, Minimally invasive surgery, McGraw Hill, N.Y., 1993). One representative application of the suture defined herein is sewing of an artificial heart valve to allow the gain of lime during surgery and reduce the risks of surgery for the patient receiving the artificial heart valve. Another representative application of the suture defined herein is its use in tissue engineering at the knee for fixation of a cartilage patch. In tissue engineering at the knee, a void of the cartilage in the knee-joint is filled by cell/scaffold structure. To fix structure, a cover in the form of a film/membrane is stitched on. This procedure is executed minimally invasive, to guide the filament and to knot the suture material is difficult. Using the suture described herein allows the use of the SM-effect to simplify the guiding of the filament and/or the knotting.

An example of the knotting process of the sutures described is given as follows. A suture described herein can be applied loosely in its temporary shape. By increasing the temperature higher than $T_{trans}$ it would shrink and tighten the knot applying the optimum force. After forming a loose knot, both ends of the suture were fixed. The knot lightened in 20 seconds when heated to 40° C. Controlling stress can be achieved, for example, on three levels: in the material itself via hard segment content, by programming, and during application via the looseness of the loops of the suture.

In one example of the knotting of the shape memory suture, a filament is knotted loosely after activating the shape memory effect. The knot is then tightened manually. This method of knotting allows the surgeon to gain of time during surgery and to adjust the tension of the knot manually and individually. In another example of the knotting of the shape memory suture, a filament is knotted loosely prior to the activation of the shape memory effect, and tightens itself with a defined tension after the shape memory effect is activated. This allows the surgeon to gain of time during surgery and to generate an accurate defined, reproducible tension of the knot.

The present invention will be further understood with reference to the following non-limiting examples.

Example 1

Smart Suture Formed of Biodegradable Shape Memory Polymer

Synthesis of Biodegradable Shape Memory Polymer In the first step of the synthesis, macrodiols with different thermal characteristics were synthesized via ring opening polymerization of cyclic diesters or lactones with a low molecular weight diol as initiator and purified according to reported methods (A. Lendlein, P. Neuenschwander, U. W. Suter, *Macromol. Chem. Phys.*, 201, 1067, (2000)). Oligo(ε-caprolactone)diol (OCL) was chosen as precursor for the switching segments (soft segments) having a melting transition temperature $T_{trans}$. Crystallizable oligo(p-dioxanone)diol (ODX) with a melting transition temperature ($T_m=T_{perm}$) was chosen as hard segment to provide the physical crosslinks. The melting transition of the latter macrodiols was determined by the average chain length which can be tailored by the monomer/initiator-ratio.

In the second step, the two macrodiols were coupled with 2,2(4),4-trimethylhexanediisocyanate as follows: both macrodiols were dissolved in 1,2-dichloroethane and heated to 80° C. An equimolar amount of 2,2(4),4-trimethylhexanediisocyanate was added. The synthesis was carried out under exclusion of water, solvents and monomers were dried by standard techniques. The crude product was precipitated in hexane.

Figure 7:
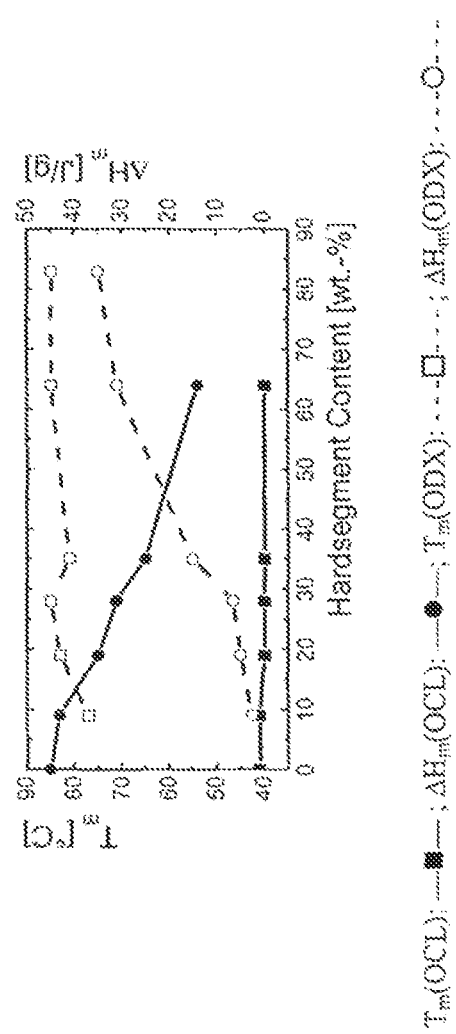
FIG. 7 shows the melting temperatures $T_m$ and enthalpies $\Delta H_m$ of multiblockcopolymers.

Property of the Biodegradable Shape Memory Polymer Hard segment contents of the synthesized polymers range from 0 to 83 wt.-% and number average molecular weights ($M_n$), which were determined by means of gel permeation chromatography relative to polystyrene standards, are between 35,000 and 77,000 with polydispersities around 2. FIG. 7 shows melting properties of multiblockcopolymers differing in their hard segment contents ($T_m$(OCL): -■-; $\Delta H_m$ (OCL): -●-; $T_m$(ODX): - - - □ - - - ; $\Delta H_m$(ODX): - - - ? - - -). Glass transition temperatures are between –51° C. and 0° C. (Table 1).

TABLE 1

Thermal properties of the multiblockcopolymers determined by dynamic mechanical analysis at varied temperature* and differential scanning calorimetry†.

| Sample ID ‖ | $T_g$(OCL)*‡ (° C.) | $T_g$(ODX)*§ (° C.) | $T_g$(ODX)† (° C.) | $\Delta c_p$(ODX)† (J·K$^{-1}$·g$^{-1}$) |
|---|---|---|---|---|
| PDC0 | −51 ± 1 | — | — | — |
| PDC9 | −51 ± 1 | −17 ± 1 | — | — |
| PDC19 | −47 ± 1 | −15 ± 1 | −18 ± 2 | 0.10 ± 0.01 |
| PDC28 | −45 ± 2 | −19 ± 1 | −24 ± 2 | 0.20 ± 0.02 |
| PDC35 | −46 ± 1 | −11 ± 1 | −17 ± 2 | 0.13 ± 0.05 |
| PDC64 | −39 ± 1 | −4 ± 1 | −17 ± 2 | 0.36 ± 0.01 |
| PDC83 | — | 0 ± 1 | −16 ± 2 | 0.60 ± 0.05 |

*DMTA: Gaba Qualimeter Eplexor, heating from –80° C. to 100° C. at 2 K·min$^{-1}$.
†DSC: Perkin-Elmer DSC 7 at 10 K·min$^{-1}$, second heating run.
‡Temperature at a maximum in E".
§Temperature at a maximum in tan δ.
†The weight content of oliga(p-dioxanone) in the polymer is given by the two-digit number in the sample ID.

The multiblockcopolymers can be elongated up to 1000% (Table 2) below they break. This allows deformations between permanent and temporary shape up to 400%, whereas the maximum deformation for Ni—Ti-alloys is 8% (J. Van Humbeeck, *Mater. Sci. Eng.* A273-275, 134 (1999)). The mechanical properties strongly depend on the hard segment content. Increasing the amount of oligo(p-dioxanone) diol in the reaction mixture leads to a stiller polymer and a decrease of the corresponding elongations at break. This can be observed at all three investigated temperatures and is due to increased crystallinity (Table 2).

TABLE 2

Mechanical properties of the multiblockcopolymers determined by tensile tests at different temperatures.*

| Sample ID† | T (° C.) | E (Mpa) | $\sigma_S$ (Mpa) | $\epsilon_S$ (%) | $\sigma_{max}$ (Mpa) | $\epsilon_{max}$ (%) |
|---|---|---|---|---|---|---|
| PDC0 | 20 | 40 ± 5 | 8 ± 1 | 33 ± 1 | 17 ± 5 | 1000 ± 150 |
| PDC9 | 20 | 34 ± 8 | 9 ± 1 | 52 ± 17 | 16 ± 1 | 1040 ± 100 |
| PDC19 | 20 | 43 ± 6 | 9 ± 1 | 40 ± 4 | 18 ± 2 | 900 ± 100 |
| PDC28 | 20 | 39 ± 5 | 8 ± 1 | 35 ± 1 | 21 ± 1 | 1100 ± 100 |
| PDC35 | 20 | 34 ± 5 | 8 ± 1 | 49 ± 2 | 13 ± 2 | 700 ± 50 |
| PDC64 | 20 | 70 ± 10 | 11 ± 1 | 37 ± 1 | 19 ± 1 | 650 ± 50 |
| PDC83 | 20 | 90 ± 30 | 15 ± 2 | 41 ± 4 | 25 ± 4 | 730 ± 50 |
| PDC0 | 37 | 17 ± 2 | 2.6 ± 0.1 | 24 ± 1 | 17 ± 1 | 1200 ± 100 |
| PDC9 | 37 | 12 ± 3 | 2.6 ± 0.3 | 33 ± 4 | 14 ± 3 | 1200 ± 170 |
| PDC19 | 37 | 14 ± 5 | 2.9 ± 0.4 | 33 ± 8 | 14 ± 1 | 1100 ± 70 |
| PDC28 | 37 | 10 ± 3 | 2.0 ± 0.4 | 32 ± 8 | 11 ± 2 | 1200 ± 70 |
| PDC35 | 37 | 15 ± 3 | 2.6 ± 0.5 | 36 ± 8 | 10 ± 2 | 800 ± 50 |
| PDC64 | 37 | 24 ± 3 | 5.5 ± 0.1 | 35 ± 6 | 12 ± 1 | 550 ± 50 |

TABLE 2-continued

Mechanical properties of the multiblockcopolymers determined by tensile tests at different temperatures.*

| Sample ID† | T (° C.) | E (Mpa) | $\sigma_S$ (Mpa) | $\epsilon_S$ (%) | $\sigma_{max}$ (Mpa) | $\epsilon_{max}$ (%) |
|---|---|---|---|---|---|---|
| PDC83 | 37 | 31 ± 4 | 6.9 ± 0.1 | 37 ± 3 | 16 ± 2 | 650 ± 60 |
| PDC0 | 50 | 0.2 ± 0.1 | — | — | 0.30 ± 0.05 | 1500 ± 200 |
| PDC9 | 50 | 0.10 ± 0.03 | — | — | 0.40 ± 0.15 | 800 ± 60 |
| PDC19 | 50 | 0.3 ± 0.1 | — | — | 0.5 ± 0.1 | 820 ± 60 |
| PDC28 | 50 | 0.9 ± 0.1 | — | — | 0.6 ± 0.1 | 740 ± 60 |
| PDC35 | 50 | 2.0 ± 0.6 | — | — | 4.0 ± 0.6 | 560 ± 60 |
| PDC64 | 50 | 9.1 ± 1.2 | — | — | 5.9 ± 1.0 | 30 ± 10 |
| PDC83 | 50 | 16.3 ± 5.7 | — | — | 8.1 ± 1.0 | 30 ± 10 |

*ZWICK Z005 WITH THERMO-CHAMBER, DEFORMATION RATE 10 MM MIN$^{-1}$.
†The weight content of oligo(p-dioxanone) in the polymer is given by the two-digit number in the sample ID.

To quantify shape memory properties, programming and recovery were investigated by cyclic thermomechanical tests as follows: the material was pressed to films having a thickness of 300-500 μm. Dog-bone shaped samples (length between clamps: 6 mm, width: 3 mm) were punched out of the films and mounted in a tensile tester equipped with a thermo-chamber (see K. Sakurai, Y. Shirakawa, T. Kahiwagi, T. Takahashi, *Polymer* 35, 4238 (1994)). The tests were carried out at 200% strain at a strain rate of 10 mm·min$^{-1}$ with $T_{low}$=−20° C. and $T_{low}$50° C. The samples were held at $T_{low}$ for 10 min before removing load (see H. Tobushi, H. Hara, E. Yamada, S. Hayashi, *S.P.I.E.* 2716, 46 (1996)).

This simple test describes shape memory in one dimension, however, the effect takes place in all three dimensions. The effect is commonly described using two important parameters. The strain fixity rate $R_f$ describes the ability of the switching segment to fix the mechanical deformation which has been applied during the programming process. For the polymers described herein, $R_f$ lies between 98% and 99.5%. The strain recovery rate $R_r$ quantifies the ability of the material to recover its permanent shape. $R_r$ depends on the cycle number and gradually approaches 100% because of reorientation of the polymer chains in the unoriented, pressed films during the early cycles, due to inelastic behavior. In the first cycle, $R_r$ has values between 76-80% for the disclosed multiblockcopolymers and reaches 98-99% in the third cycle. Ni—Ti-alloys show stresses in the range of 200-400 MPa during shape memory transition whereas the shape memory thermoplastics produce stresses in the range between 1 and 3 MPa depending on the hard segment content (H. Tobushi, S. Hayashi, A. Ikai, H. Hara, *J. de Physique IV* 6, C1-377 (1996)). The lower value for shape memory polymers resembles the mechanical stresses in soft tissue (see A. F. T. Mak, M. Zhang, in *Handbook of Biomaterial Properties*, J. Black, G. Hastings, Eds. (Chapman & Hall, N.Y., ed. 1, 1998) pp. 66-69).

Figure 8:
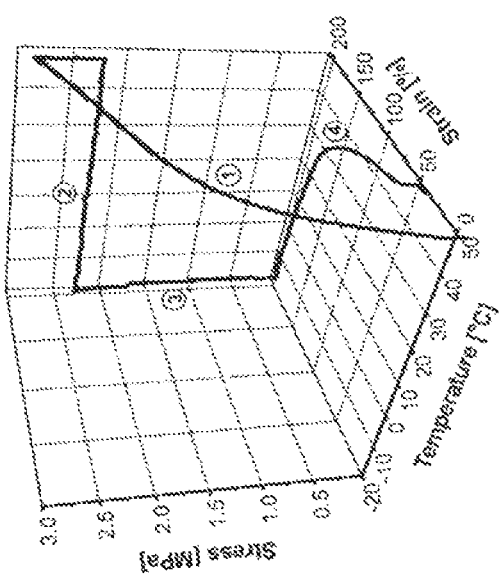
FIG. 8 shows the cyclic thermomechanical experiment of a shape memory multiblock copolymer PDC35 with $T_{trans}$=40° C.

To record the change in elongation during the shape memory effect, another cyclic thermomechanical experiment was performed according to the process as illustrated by FIG. 8. Step 1 is the deformation of the permanent shape and corresponds to a standard stress-strain test. After maintaining this strain for 5 minutes to allow relaxation for chains, the stress is then held constant while the sample is cooled (step 2) whereby the temporary shape is fixed. Then stress is completely removed after waiting for 10 minutes (step 3) and the sample is then set in its temporary shape. Heating up in step 4 (2 K·min$^{-1}$) actuates the shape memory effect. The contraction of the sample can be observed on the strain axis and the fastest shape change is recorded at $T_{trans}$=40° C. Table 3 shows selected shape memory properties determined from cyclic thermo-mechanical experiments.

TABLE 3

Selected shape memory properties determined from cyclic thermo-mechanical experiments between $T_{low}$ = −20° C. and $T_{high}$ = 50° C.*

| | | PDC9† | | PDC28† | | PDC35† | |
|---|---|---|---|---|---|---|---|
| N | $\epsilon_{PROG}$ (%) | $R_R$ (%) | $R_F$ (%) | $R_R$ (%) | $R_F$ (%) | $R_R$ (%) | $R_F$ (%) |
| 1 | 200 | 76.0 | 99.5 | 79.0 | 99.0 | 80.0 | 98.0 |
| 2 | 200 | 89.0 | 99.5 | 93.5 | 99.0 | 89.5 | 98.0 |
| 3 | 200 | 99.0 | 99.5 | 96.0 | 99.0 | 98.0 | 98.0 |
| 4 | 200 | 99.0 | 99.5 | 99.0 | 99.0 | 99.0 | 98.0 |

*Zwick Z005 with thermo-chamber, deformation rate 10 mm min$^{-1}$.
†The weight content of oligo(p-dioxanone) in the polymer is given by the two-digit number in the sample ID.

Figure 9:
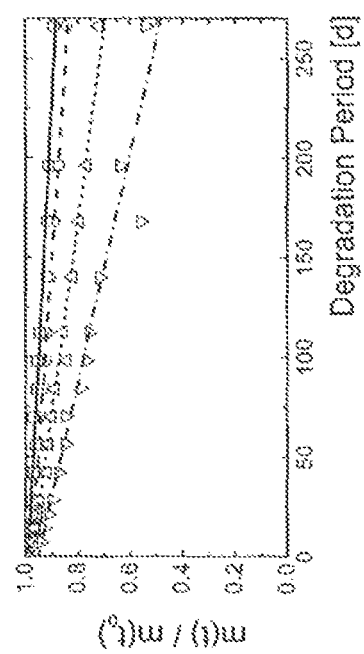
FIG. 9 shows the hydrolytic degradation of thermoplastic shape memory elastomers in aqueous buffer solution (pH 7) at 37° C.

Degradation Kinetics. The degradation kinetics was investigated. As shown in FIG. 3, the degradation kinetics of the disclosed polymer can be controlled via composition and relative mass content of the precursor macrodiols. FIG. 9 shows that an increase in the ODX-content leads to a faster loss in mass, since the concentration of rapidly hydrolyzable ODX-ester bonds in the amorphous phase is increased (O: PDC10; □: PDC17; Δ: PDC31; ∇: PDC42). Relative mass loss for multiblockcopolymers differs in relation to their respective hard segment content. The multiblockcopolymers presented here show linear mass loss in vitro (FIG. 9), resulting in a continuous release of degradation products.

In vitro test of biocompatibility The tissue-compatibility of the polymers described herein was investigated using chorioallantoic membrane tests (CAM-tests) which are a sensitive method to evaluate toxicity (K. Spanel-Borowski, *Res. Exp. Med. (Berl)* 189, 69 (1989)). Nine separate experiments were carried out. All tests showed good tissue-compatibility when graded according to Folkman (R. Crum, S. Szabo, J. Folkman, *Science* 230, 1375 (1985)). The test results showed that there was no detectable change in the number or shape of blood vessels or damage under or in the vicinity of the polymer film (sample length: left ~0.3 cm, right ~0.5 cm). For a positive control sample, see A. Lendlein, *Chem. in unserer Zeit* 33, 279 (1999).

In vitro test of the tying of suture knot The highly elastic shape memory thermoplastics were extruded into monofilaments by extrusion at 90° C. through a 1 mm rod die on a Haake Polylab single-screw extruder. A suture sterilized with ethylene oxide at 45° C. was programmed under sterile conditions by exerting a controlled stress on the extruded fiber and subsequent thermal quenching. This smart suture was tested in the following animal model: A rat (WAG; weight 250 g; albino) was sacrificed and shaved. An incision through the belly tissue and the abdominal muscle was made. The wound was loosely sutured using a standard surgical needle (Hermann Butsch GmbH, size 15, ⅜ circle). With an increase in temperature to 41° C. the shape memory effect was actuated. The shrinkage of the fiber while temperature increases was shown in an animal experiment. This test was carried out four times using two different animals. For these tests the fibers were elongated by 200% during programming, and were able to generate a force of 1.6 N upon actuating the shape memory effect in vitro. During the animal experiment, 0.1 N could be detected in the surrounding tissue. The force of the fiber was determined with a tensile tester equipped with thermo-chamber. The force on the surrounding tissue was estimated by mounting a spring of known stiffness close to the wound and measuring the length change.

Modifications and variations of the polymeric compositions and methods of preparation and use thereof will be obvious to those skilled in the art from the foregoing detailed description. Such modifications and variations are intended to come within the scope of the appended claims.

We claim:

1. A suture having shape memory capability comprising a multifilament comprising a combination of biodegradable filaments and of non-biodegradable filaments,
   wherein the biodegradable filaments are formed of a material comprising a biodegradable shape memory polymer composition wherein the composition comprises:
   a) at least one hard segment which has a $T_{trans}$ between −40 and 270° C.,
   b) at least one soft segment which has a $T_{trans}$ at least 10° C. lower than that of the hard segment(s), which is linked to at least one hard segment,
   wherein at least one of the hard or soft segments includes a biodegradable region or at least one of the hard segment(s) is linked to at least one of the soft segment(s) through a biodegradable linkage, and
   wherein the non-biodegradable filaments are formed of a material comprising a non-biodegradable shape memory polymer composition wherein the composition comprises:
   c) at least one hard segment which has a $T_{trans}$ between −40 and 270° C.,
   d) at least one soft segment which has a $T_{trans}$ at least 10° C. lower than that of the hard segment(s), which is linked to at least one hard segment.

2. A suture of claim 1 capable of forming a self-tightening knot.

3. A suture of claim 1 comprising a coating capable of altering the degradation of the biodegradable shape memory polymer composition.

4. A suture of claim 1 comprising a coating comprising a shape memory polymer composition.

5. A suture of claim 1 comprising a coating selected from the group consisting of a covalent shape memory network and a thermoplastic.

6. The suture of claim 1 wherein the suture assumes a deformed shape caused by the biodegradable shape memory filament; and is capable of reversing the deformed shape to give a non-deformed shape by degradation of the biodegradable shape memory filament.

7. The suture of claim 1 wherein the biodegradable filaments and non-biodegradable filaments are all programmed substantially alike.

8. The suture of claim 1 wherein the biodegradable filaments and non-biodegradable filaments are all programmed substantially differently.

9. The suture of claim 1 wherein the ratio of the number of filaments of biodegradable shape memory material over filaments of non-biodegradable shape memory material is in the range of 0.5/99.5 to 99.5/0.5.

10. The suture of claim 1 further comprising an agent selected from the group consisting of therapeutic, diagnostic and prophylactic agents.

11. The suture of claim 10 wherein the agent is selected from the group consisting of a disinfectant and an antibiotic.

12. A suture having shape memory capability comprising a multifilament comprising a combination of biodegradable filaments and of non-biodegradable filaments,
    wherein the biodegradable filaments are formed of a material comprising a biodegradable shape memory polymer composition wherein the composition comprises:
    a) at least one hard segment which has a $T_{trans}$ between −40 and 270° C.,
    b) at least one soft segment which has a $T_{trans}$ at least 10° C. lower than that of the hard segment(s), which is linked to at least one hard segment,
    wherein at least one of the hard or soft segments includes a biodegradable region or at least one of the hard segment(s) is linked to at least one of the soft segment(s) through a biodegradable linkage, and
    wherein the non-biodegradable filaments are formed of a material comprising a non-biodegradable shape memory polymer composition wherein the composition comprises:
    c) at least one hard segment which has a $T_{trans}$ between −40 and 270° C.,
    d) at least one soft segment which has a $T_{trans}$ at least 10° C. lower than that of the hard segment(s), which is linked to at least one hard segment, and
    wherein the suture assumes a deformed shape fixed by the biodegradable shape memory filament; and is capable of reversing the deformed shape to give a non-deformed shape by degradation of the biodegradable shape memory filament.

* * * * *